(12) United States Patent
Lu

(10) Patent No.: US 7,325,702 B2
(45) Date of Patent: Feb. 5, 2008

(54) ORTHOPAEDIC PASTE DELIVERING TOOL AND METHOD FOR CONTINUALLY DELIVERING THE PASTE

(76) Inventor: Pong-Jeu Lu, 8F.-4, No. 88, Sec. 3, Changrong Rd., Tainan City 701 (TW)

( * ) Notice: Subject to any disclaimer, the term of this patent is extended or adjusted under 35 U.S.C. 154(b) by 272 days.

(21) Appl. No.: 11/152,170

(22) Filed: Jun. 15, 2005

(65) Prior Publication Data

US 2006/0283890 A1    Dec. 21, 2006

(51) Int. Cl.
  *B67D 5/54*    (2006.01)
(52) U.S. Cl. .......................... 222/1; 222/326; 222/389
(58) Field of Classification Search ................ 222/326, 222/327, 387, 388, 389, 1
  See application file for complete search history.

(56) References Cited

U.S. PATENT DOCUMENTS 4,842,167 A * 6/1989 Fornasari .................... 222/249
5,172,835 A * 12/1992 Hudcovic et al. ........... 222/380
5,435,462 A *  7/1995 Fujii ............................ 222/82
5,816,445 A * 10/1998 Gardos et al. ................. 222/1
5,816,455 A * 10/1998 Alpers et al. ............... 222/388

* cited by examiner

*Primary Examiner*—Joseph A. Kaufman
(74) *Attorney, Agent, or Firm*—Bacon & Thomas, PLLC

(57) ABSTRACT

The present invention discloses a technique for continually delivering an orthopaedic paste into a bone, which will harden in the bone and act as a medical implant. The present invention uses a replacement mechanism in delivering the paste stored in a chamber through a tube in fluid communication with the chamber, which includes invading the paste in the chamber with a small volume of recovery member such as a rod to replace the same volume of paste into the tube, and retreating the invading rod while applying a pressure to the paste in the chamber, so that a space created by the retreating is replaced by the paste, and repeating the invasion and the retreating alternately to continually delivere the paste through the tube.

18 Claims, 3 Drawing Sheets

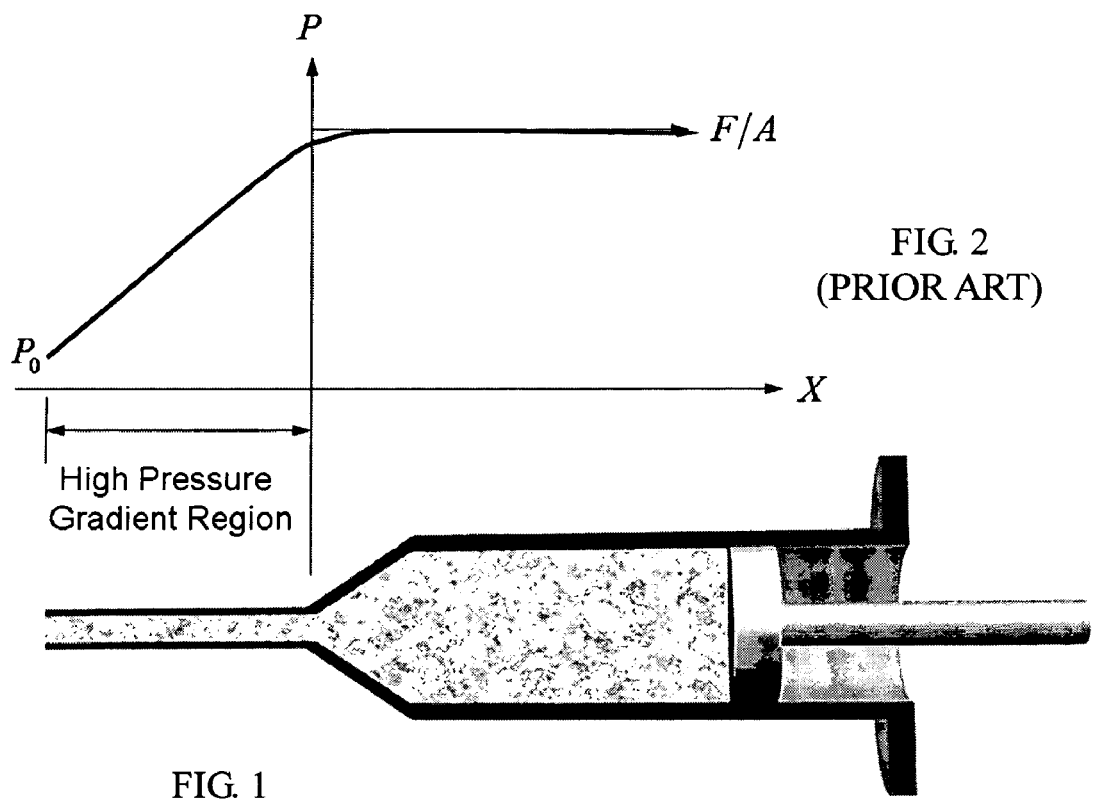
FIG. 2
(PRIOR ART)
FIG. 1
(PRIOR ART)
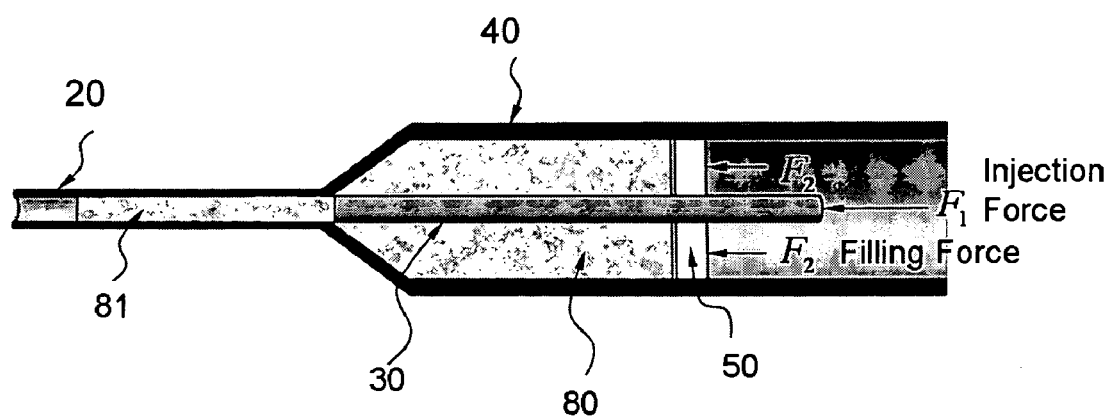
FIG. 3

ORTHOPAEDIC PASTE DELIVERING TOOL AND METHOD FOR CONTINUALLY DELIVERING THE PASTE

FIELD OF THE INVENTION

The present invention is related to a technique for delivering an orthopaedic paste into a bone, which will harden in the bone and act as a medical implant. The orthopaedic paste can be any known flowable orthopaedic filling material including, for example, a liquid-powder mixture and a viscous liquid containing a polymeric material.

BACKGROUND OF THE INVENTION

FIG. 1 shows a scheme of a common method of delivering an orthopaedic paste from a container to a designated spot (bone cavity) through a thin tube. In general, the orthopaedic paste, which is a liquid-solid two-phase mixture stored in a container or reservoir, is intended to be transported through a thin tube into a designated spot in a bone structure, tissue or organ of a diseased subject. Conventionally used is a tapered cone-cylinder design which connects the container and the thin tube (syringe), wherein a driving force is applied for orthopaedic paste delivery. For this one-step, direct forced-filling method, the liquid and powder of the orthopaedic paste would tend to separate upon the exertion of the force during the filling process. The underlying physics is explained below.

Generally speaking, the speed of delivery is slow for the method illustrated in FIG. 1. The physical condition occurring in the container throughout the filling process can be described using a static equilibrium concept. The internal pressure developed is approximately equal to the applied force divided by the surface area of the back plate, namely, F/A. This pressure (P) is almost uniformly distributed everywhere except around the exit region of the container, i.e. the region near to the thin tube, where the pressure drops drastically to the ambient pressure ($P_0$) of the designated spot, as shown in FIG. 2. This locally developed pressure gradient around the junction of the container and the tube forms the major mechanism that drives the fluid portion of the orthopaedic paste mixture out of the tiny orifice of the container. This can be illustrated by the incompressible Navier-Stokes equation of motion for a fluid flow, $$\underbrace{\rho \frac{\partial u}{\partial t}}_{unsteady} + \underbrace{\rho u \frac{\partial u}{\partial x} + \rho v \frac{\partial u}{\partial y}}_{convection} = -\underbrace{\frac{\partial p}{\partial x}}_{\substack{pressure \\ gradient}} + \underbrace{\mu \left( \frac{\partial^2 u}{\partial x^2} + \frac{\partial^2 u}{\partial y^2} \right)}_{\substack{viscous \\ effects}}$$

In which, $\rho$, u, v, p and $\mu$ are respectively the density, velocity components, pressure and viscosity of the fluid, and (x, y, t) are the Cartesian and time coordinates. The orthopaedic paste delivery motion is in general very slow so the unsteady and convection terms can be neglected, resulting in a balance of the pressure gradient and the viscous terms. In other words, the locally developed pressure gradient drives the fluid motion by overcoming the internal or wall friction as the fluid is ejected out. Owing to the large solid-liquid density ratio, the speed of the fluid usually exceeds that of the solid particles, causing the separation of the orthopaedic paste constituents. The fluid part of the orthopaedic paste will continuously flow out of the container because of the continuity characteristic of the flow motion. Nevertheless, the solid part of the orthopaedic paste experiences different physical mechanism as the force is applied. In the beginning, a diluted orthopaedic paste is ejected because more liquid than solid part is compressed out of the container. The remaining orthopaedic paste gets drier during the pressurization period. The small exit area prohibits the dried solid particles from moving quickly out of the container. Except for the initial powder that drifts out of the container with the carrier liquid, the remainder powder of the orthopaedic paste will be closely packed or interlocked together, resulting in a static equilibrium chunk due to the loss of fluidity. This liquid-solid separation mechanism explains why the one-step, direct forced-filling device often fails as a satisfactory orthopaedic paste delivery injector, especially for a minimally invasive surgical procedure.

SUMMARY OF THE INVENTION

A primary object of the present invention is to provide a tool and method for continually delivering an orthopaedic paste stored in a chamber into a bone through a tube.

Another object of the present invention is to provide a tool and method for delivering an orthopaedic paste stored in a chamber into a bone through a tube in the absence of a pressure build-up in the chamber during the delivery.

Still another object of the present invention is to provide a tool and method for delivering an orthopaedic paste comprising particles and liquid into a bone through a tube without significantly changing the solid/liquid ratio of the paste dispensed through the tube.

In order to accomplish the aforesaid objects of the present invention, a replacement mechanism is used in delivering the paste stored in the chamber through a tube in fluid communication with the chamber, which includes invading the paste in the chamber with a small volume of recovery member such as a rod to replace the same volume of paste into the tube, and retreating the invading rod while applying a pressure to the paste in the chamber, so that a space created by the retreating is replaced by the paste, and repeating the invasion and the retreating alternately.

BRIEF DESCRIPTION OF THE DRAWINGS

FIG. 1 is a schematic partial cross-sectional view of the prior art one-step, direct forced-filling orthopaedic paste tool.

FIG. 2 shows a pressure profile in the paste advance direction (X) of the prior art one-step, direct forced-filling orthopaedic paste tool shown in FIG. 1.

FIG. 3 is a schematic partial cross-sectional view of a horizontal two-step orthopaedic paste feeding device of the present invention.

DETAILED DESCRIPTION OF THE INVENTION

Figure 4:
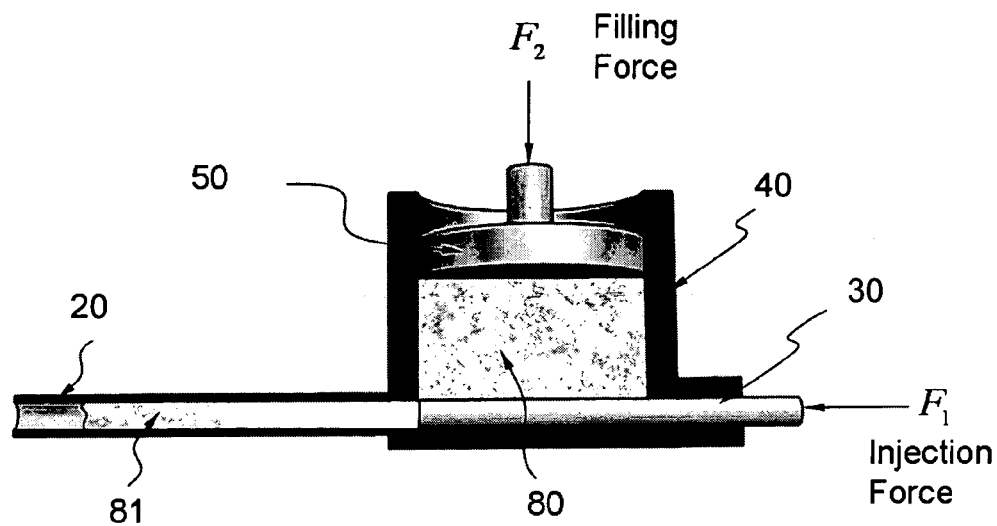
FIG. 4 is a schematic partial cross-sectional view of a vertical two-step orthopaedic paste feeding device of the present invention.

An orthopaedic paste delivering cool, in one embodiment, comprises:
a chamber for storing an orthopaedic paste,
a tube in fluid communication with the paste stored in the chamber, a recovery member movably received in a hole provided on a wall of the chamber, which can be pushed to move from a first position to a second position, so that a portion of the recovery member invades the paste stored in the chamber, and thus the paste enters the tube in an amount substantially equivalent to a volume of the invading portion of the recovery member, and a press member in contact with the paste stored in the chamber, which presses the paste stored in the chamber to eliminate a space created in the chamber when the recovery member is being pulled from the second position to the first position.

In one embodiment, the recovery member is a rod having a diameter less than 20 times of an inner diameter of the tube. For example, the rod may have a diameter ranging from 5 times of the inner diameter of the tube to smaller than the inner diameter of the tube.

The press member may be a plate slidably received in the chamber, wherein one side of the plate is in contact with the paste stored in the chamber and the other side of the plate is adapted to receive a positive pressure source.

The weight of the plate, the positive pressure source, or both contribute a drive to the pressing of the paste by the press member.

In certain embodiments, the weight of the plate, the positive pressure source or a combination of them are not enough to cause a significant amount of the paste stored in the chamber entering the tube.

The orthopaedic paste delivering tool may further comprise a driving means for reciprocally performing the pushing and pulling of the recovery member.

For example, the driving means may comprise a pneumatic cylinder.

A method for delivering a paste comprises steps of:

filling a chamber with a paste, with which a tube is in fluid communication, pressing the paste in the chamber with a pressure which is not enough to cause a significant amount of the paste in the chamber entering the tube, reciprocally pushing a recovery member to invade the paste in the chamber and pulling the invading recovery member in the chamber, so that the paste enters the tube in an amount substantially equivalent to a volume of an invading portion of the recovery member as a result of said pushing, and that a space created in the chamber by said pulling is eliminated as a result of said pressing, and thus the paste in the chamber is continually delivered through said tube.

In one embodiment, the recovery member is a rod having a diameter less than 20 times of an inner diameter of the tube.

For example, the rod may have a diameter ranging from 5 times of the inner diameter of the tube to smaller than the inner diameter of the tube.

The pressing may be carried out by using a press member slidably received in the chamber, wherein one side of the press member is in contact with the paste stored in the chamber and the other side of the press member is adapted to receive a positive pressure source.

The press member may be, for example, a plate.

The weight of the plate and/or the positive pressure source may contribute a drive to the pressing.

In certain embodiments, the reciprocal pushing and pulling of the recovery member may be carried out by suing a pneumatic cylinder.

The recovery member may be arranged to be pushed to invade the paste in the chamber without entering the tube during said pushing.

The paste may be, for example, a liquid-powder mixture having a liquid to solid ratio by volume from about 0.1 to 10, such as a viscous liquid comprising a polymeric material, which has a viscosity greater than about 500 centipoise.

The orthopaedic paste delivery process of the present invention can be facilitated using a novel two-step method described below. FIGS. 3 and 4 depict two representative designs, namely, the horizontal and vertical feeding devices [Note: Other angles are also possible]. In both designs a thin injection (outlet) tube 20 is connected to one end of a storage container 40 with a back plate 50 being placed over the other end for pressurization. An injection rod 30 is used for pushing the orthopaedic paste 80 into the outlet tube 20. In the forward stroke motion, an orthopaedic paste segment 81 is pushed into the tube. As the rod 30 is withdrawn, a low-pressure void column will be generated accompanying the rearward stroke motion of the rod 30. The surrounding orthopaedic paste will immediately fill this void column space due to a "vacuum suction" effect as well as the applied back pressure. Unlike the conventional one-step design shown in FIG. 1, the present applied filling force ($F_2$) or the pressure gradient developed is usually small, which is required only for pressing the orthopaedic paste into the void space created by the previous back stroke. Separation of the orthopaedic paste injection and feeding into different steps with small applied injection and filing forces ($F_1$, $F_2$) characterizes the present design philosophy. The orthopaedic paste feeding step follows the injection step, and the assigned delivery mission is accomplished by an accumulation of the delivered orthopaedic paste segments 81. In both steps the aforementioned high pressure gradient phenomenon would not occur and these two steps can be repeatedly operated. There is literally no limitation on the amount of the orthopaedic paste to be delivered. Moreover, the force applied on the injection rod can be adjusted to overcome the resisting pressure exerted on the outlet end of the tube.

Contrary to the device depicted in FIG. 1, the container shape for the two-step method is not critical. In principle, any shape and orientation of the container 40 can be used. This is due to the advantage generated by the present design since, for any container shape, the applied force can easily feed the orthopaedic paste into the void space created by the previous injection stroke partly due to the aforementioned vacuum suction effect.

The two-step orthopaedic paste delivery system of the present invention consists essentially of four structural components and two external forcing mechanisms. The function of each constituent part is described in the following with reference to FIG. 4.

1. Orthopaedic Paste Storage Container 40

The container is used to store the orthopaedic paste to be delivered. The inner wall can be a cylinder of any cross sectional shapes. Surface roughness of the inner wall should be minimized to reduce wall friction. Non-stick coating may also be used to further enhance the feeding effectiveness.

2. Injection (outlet) Tube 20

This tube is preferably a substantially constant cross sectional tube, which can be either flexible or rigid. Orthopaedic paste segments will be delivered through this tube into the designated delivery spot.

3. Injection Rod 30

This injection rod has substantially the same cross sectional shape (or a modified shape) as the injection tube 20. The length of the injection rod is selected in such a way that, in the forward stroke, the rod end barely touches the entrance plane of the injection tube 20. For this motion mode, the diameter of the injection rod can be larger than the inner diameter of the injection tube. Practically, the injection rod should have a diameter not too larger than the inner diameter of the injection tube. Preferably, the injection rod should not have a diameter larger than the inner diameter of the injection tube by five times; and more preferably, the injection rod should not have a diameter larger than the inner diameter of the injection tube by three times. For another motion mode, the injection rod may be partly inserted into the injection tube. In this case, the diameter of the injection rod should be a little smaller than the inner diameter of the injection tube. Clearance can be properly selected to facilitate the stroke motion of the injection rod. The length of the rod can vary, depending on how much orthopaedic paste is intended to be left in the injection tube beyond the designated delivery spot.

4. Back Plate 50

Back plate is used for transmitting the pressure required to feed the orthopaedic paste into the void column created by the previous back stroke as well as to prevent the spillage of the orthopaedic paste during the feeding process.

5. Orthopaedic Paste Delivery Mechanism (not shown in the drawings) for providing the injection force $F_1$ This mechanism can be any manually, pneumatically, hydraulically, or electro-magnetically driven devices. The force $F_1$ applied should be greater than or equal to the sum of the resisting load occurring at the delivery spot plus the friction force exerted by the outlet tube wall. Control can be applied to facilitate the reciprocal motion of the injection rod connected to this forcing mechanism.

6. Orthopaedic Paste Feeding Mechanism (not shown in the drawings) for providing the feeding force $F_2$ This mechanism can be any manually, pneumatically, hydraulically, or electro-magnetically driven devices. The applied force $F_2$ should be adjusted barely enough to feed but not overly compress the orthopaedic paste contained inside the container. The feeding is largely assisted by a vacuum suction effect induced by the rearward stroke of the injection rod, which creates a low-pressure void column space.

In view of the above, the present invention has at least the following major features:
1. The separation of orthopaedic paste delivery into two uncorrelated (independent) steps of feeding and injection.
2. Orthopaedic paste injection is accomplished without a locally developed high pressure gradient.
3. Orthopaedic paste feeding is accomplished by filling the low-pressure void column space assisted by a vacuum suction effect which is a separate (irrelevant) motion to the orthopaedic paste injection
4. Total orthopaedic paste delivery is accomplished by a series of reciprocal injection and feeding strokes rather than the one-step, direct forced-filling process.

An orthopaedic paste delivery tool constructed according to one of the preferred embodiments of the present invention is described in the following with reference to FIGS. 5 and 6.

Figure 5:
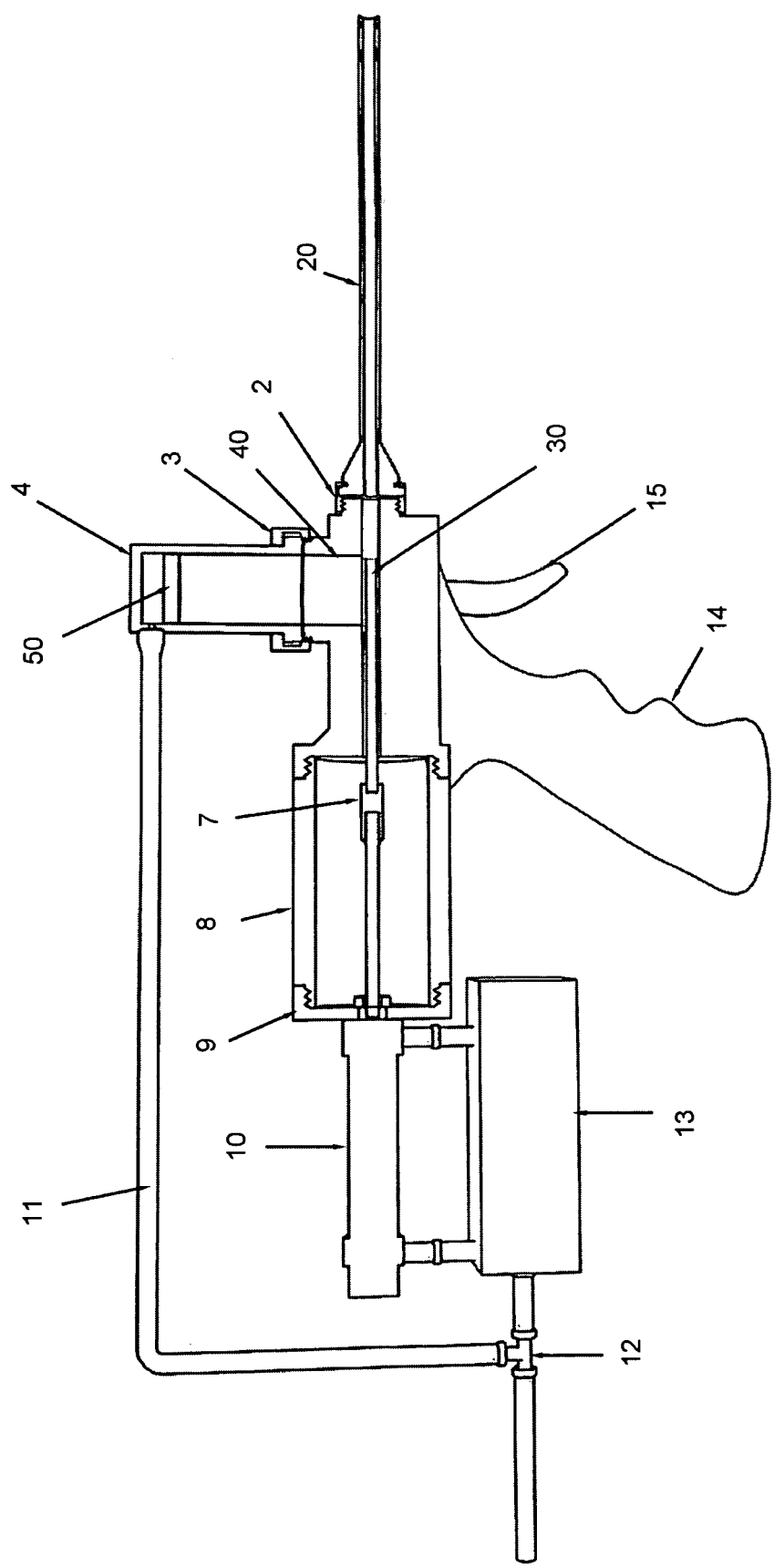
FIG. 5 is a schematic cross-sectional view of a vertical two-step orthopaedic paste feeding tool of the present invention.

The orthopaedic paste delivery tool depicted in FIG. 5 mainly consists of four modules: 1) Injection Tube; 2) Main Body; 3) Pneumatic Driver; and 4) Controller. For each module the function and components included are described as follows.

1. Injection Tube 20

This tube 20 is the access channel for the orthopaedic paste to be delivered to the designated place in the diseased subjects. The diameter of the tube 20 is around 1-3 mm, preferably 2-3 mm, and the material adopted could be stainless steel or other metal or polymers. One end of this tube is attached to the main body module via a quick connector 2. This injection tube 20 could be disposable after orthopaedic paste delivery. Quick connector 2 eases the attachment and detachment of the tube 20 to and from the main body module. Upon finishing orthopaedic paste delivery, by unscrewing the quick connector 2, the injection tube 20 can be detached from the rest heavy modules for orthopaedic paste solidification. A pushing rod can be inserted from behind the tube end to further add the remaining orthopaedic paste in the tube to the cavity.

2. Main Body Module

This module connects respectively the injection tube 20, feeding cup 4 and the pneumatic driver module. This module is secured on a handle 14 for the operator to easily accomplish the orthopaedic paste delivery mission. Orthopaedic paste is stored in advance in the feeding cup 4 which is mounted onto and off a storage container 40 provided on the main body via a quick connector 3. At the base of the feeding cup lie a back plate 50 and a through hole connected to the pneumatic line 11. Pressurized air is supplied through the pneumatic line 11 into the feeding cup 4. The back plate 50 then works as the interface to exert pressure on the orthopaedic paste for feeding. Sealing is applied around the rim of the back plate 50 as well as at the quick connector 3 base so as to maintain the feeding pressure and keep the air from leakage. An orthopaedic paste injection rod 30, as propelled by the pneumatic driver, works back-and-forth at the bottom of the container 40 as a driving force to push the orthopaedic paste segment into the injection tube 20. The length of the injector rod 30 is selected in such a way that, in the forward stroke, the rod end barely touches the entrance plane of the injection tube 20. This design length can avoid the back spillage of the orthopaedic paste in the injection tube as the injector is withdrawn in the backward stroke. In order to facilitate orthopaedic paste feeding, the inner wall of the feeding cup 4 can be properly configured and/or coated with non-sticking materials.

3. Pneumatic Driver Module

This module uses a pneumatic cylinder 10 and directional control valve 13 which are commercially available components. Since in general the size of the stroke rod of the pneumatic cylinder 10 is different from that of the injection rod 30, an adaptor 7 is used to connect together the pneumatic cylinder 10 and the injection rod 30, allowing power transmitted from the air supply to the delivered orthopaedic paste. The stroke distance determines the model type of the pneumatic cylinder selected. In order to fix the pneumatic cylinder 10 and the directional control valve 13 firmly onto the main body, a connector 8 and connector cap 9 are used. Note that the connections at the two ends of this connector structure should be air tight so as to assure the feeding pressure desired. Pressurized air enters the pneumatic cylinder 10 as well as the feeding cup 4 through a two-way connector 12. This pressure supply can be adjusted in accordance with the resisting pressure at the cavity where orthopaedic paste is intended to be placed. The directional control valve 13 is an electromagnetic valve which can be used to control the air ways inside the pneumatic cylinder 10. As the air way is selected by the electromagnetic circuit, the rod of the pneumatic cylinder will be actuated in either forward or backward movement.

4. Controller 60

Figure 6:
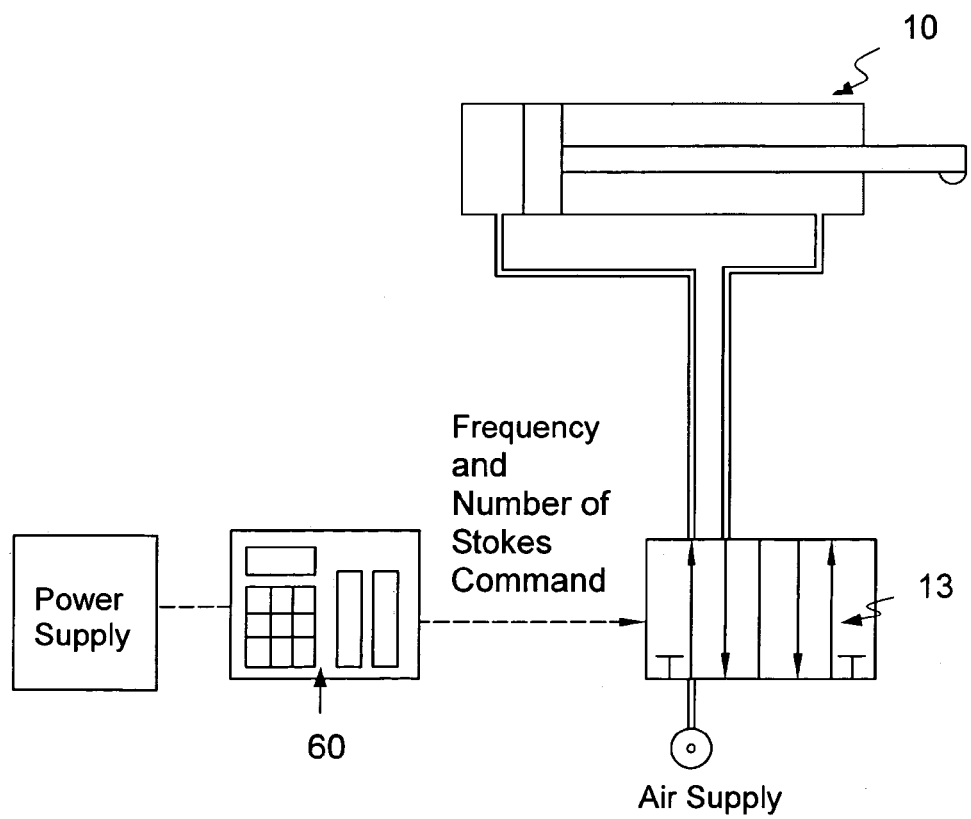
FIG. 6 is a schematic diagram showing the control loop for orthopaedic paste injection used in the tool shown in FIG. 5.

The controller layout is illustrated in FIG. 6. The controller 60 is a circuit board which is designed according to the operational requirements. Presently the control parameters are the stroke frequency and the total number of strokes. The control command can be sent to the directional control valve 13 via an electric circuit together with an ON/OFF trigger 15 mounted on the handle 14. As the trigger 15 is pressed down, the control command will be activated to drive the injection rod 30 moving back-and-forth with a preset frequency and total number of strokes. The feeding motion can be stopped as required when the trigger 15 is released to spring back and the control command gets cut off. The air ways regulated by the directional control valve 13 is also sketched in FIG. 6. The left air way is a route for pushing the injector rod forward and vice versa for the right air way. The amount of orthopaedic paste to be delivered can be calibrated and decided by the specified number of strokes. The feeding frequency, however, is determined by the resisting pressure and the orthopaedic paste setting time. Generally, the higher the resisting pressure, the slower the feeding frequency because the time required for the exertion of force to move the injector rod will increase. For a fast-setting orthopaedic paste the feeding frequency should be higher and the air supply pressure should be raised accordingly.

The invention claimed is:

1. The orthopaedic paste delivering tool comprising:
a chamber for storing an orthopaedic paste;
a tube in fluid communication with the paste stored in the chamber;
a recovery member movably received in a hole provided on a wall of the chamber, which can be pushed to move from a first position to a second position, so that a portion of the recovery member invades the paste stored in the chamber, and thus the paste enters the tube in an amount substantially equivalent to a volume of the invading portion of the recovery member; and
a press member in contact with the paste stored in the chamber, which presses the paste stored in the chamber to eliminate a space created in the chamber when the recovery member is being pulled from the second position to the first position.

2. The tool as defined in claim 1, wherein the recovery member is a rod having a diameter less than 20 times of an inner diameter of the tube.

3. The tool as defined in claim 2, wherein the rod has a diameter ranging from 5 times of the inner diameter of the tube to smaller than the inner diameter of the tube.

4. The tool as defined in claim 1, wherein the press member is a plate slidably received in the chamber, and one side of the plate is in contact with the paste stored in the chamber and the other side of the plate is adapted to receive a positive pressure source.

5. The tool as defined in claim 4, wherein weight of the plate, the positive pressure source, or both, contribute a drive to said pressing.

6. The tool as defined in claim 5, wherein the weight of the plate, the positive pressure source or a combination of them are not enough to cause a significant amount of the paste stored in the chamber entering the tube.

7. The tool as defined in claim 1 further comprising a driving mean for reciprocally performing the pushing and pulling of the recovery member.

8. The tool as defined in claim 7, wherein said driving means comprises a pneumatic cylinder.

9. A method for delivering a paste comprising the following steps:
filling a chamber with a paste, with which a tube is in fluid communication;
pressing the paste in the chamber with a pressure which is not enough to cause a significant amount of the paste in the chamber entering the tube;
reciprocally pushing a recovery member to invade the paste in the chamber and pulling the invading recovery member in the chamber, so that the paste enters the tube in an amount substantially equivalent to a volume of an invading portion of the recovery member as a result of said pushing, and that a space created in the chamber by said pulling is eliminated as a result of said pressing, and thus the paste in the chamber is continually delivered through said tube.

10. The method as defined in claim 9, wherein the recovery member is a rod having a diameter less than 20 times of an inner diameter of the tube.

11. The method as defined in claim 10, wherein the rod has a diameter ranging from 5 times of the inner diameter of the tube to smaller than the inner diameter of the tube.

12. The method as defined in claim 9, wherein said pressing is carried out by using a press member slidably received in the chamber, wherein one side of the press member is in contact with the paste stored in the chamber and the other side of the press member is adapted to receive a positive pressure source.

13. The method as defined in claim 12, wherein said pres member is a plate.

14. The method as defined in claim 13, wherein weight of the plate, the positive pressure source, or both, contribute a drive to said pressing.

15. The method as defined in claim 9, wherein said reciprocally pushing and pulling driving is carried out by using a pneumatic cylinder.

16. The method as defined in claim 9, wherein said recovery member is pushed to invade the paste in the chamber without entering the tube during said pushing.

17. The method as defined in claim 9, wherein said paste is a liquid-powder mixture having a liquid to solid ratio by volume from about 0.1 to 10.

18. The method as defined in claim 9, wherein said paste is a viscous liquid comprising a polymeric material, which has a viscosity greater than about 500 centipoise.

* * * * *